United States Patent [19]

Burnap

[11] 4,017,619
[45] Apr. 12, 1977

[54] ANESTHETIC AND SEDATIVE COMPOSITION

[76] Inventor: Raymond W. Burnap, 1528 Canada Blvd., Glendale, Calif. 91208

[22] Filed: Sept. 29, 1975

[21] Appl. No.: 617,971

Related U.S. Application Data

[63] Continuation of Ser. No. 409,893, Oct. 26, 1973, abandoned.

[52] U.S. Cl. .............................. 424/244; 424/330
[51] Int. Cl.² ...................................... A61K 31/33
[58] Field of Search ........................ 424/330, 244

[56] References Cited
OTHER PUBLICATIONS

PDR, 27 Ed., Medical Economics Co., Overdell, N.J., (5-8-73), pp. 610-612.

*Primary Examiner*—Jerome D. Goldberg
*Attorney, Agent, or Firm*—Fulwider, Patton, Rieber, Lee & Utecht

[57] ABSTRACT

An anesthetic and sedative composition comprising a mixture of ketamine hydrochloride and diazepam is disclosed. The ratio of ketamine hydrochloride to diazepam is 10:1. As administered in anesthetic or sedative doses patients exhibit no deleterious reduction in respiration, blood pressure or heart action and patients are unable to recall any unpleasant psychological experiences associated with the administration of the composition.

1 Claim, No Drawings

ANESTHETIC AND SEDATIVE COMPOSITION

This application is a continuation of prior application Ser. No. 409,893 filed on Oct. 26, 1973 for ANESTHETIC AND SEDATIVE COMPOSITION which is now abandoned in favor of the instant application.

BACKGROUND OF THE INVENTION

This invention relates to an anesthetic and sedative composition.

Many compositions are available for sedating patients or, in larger dosages, for inducing surgical anethesia in patients. These materials are used above or in combination with other agents, such as nitrous oxide, to induce narcosis and to raise the patients pain threshold so that the patient can withstand surgical procedures. Likewise in smaller doses, these materials can reduce anxiety and generally sedate the patient. For example the following compounds are in general use as sedative and anesthetic agents: thiopental sodium, 5-allyl-1-methyl-5-(1-methyl-2-pentynyl) barbituric acid sodium salt (brevitol), 2-bromo-2-chloro-1,1,1-trifloroethane (halothane), and the like.

Most anesthetic and sedative agents, in addition to their beneficial effects, also lower certain body functions, such as respiration, blood pressure and heart action. Lowered body functions may sometimes lead to complications, particularly in older patients and in patients suffering from cardiac and vascular diseases and diseases of the kidneys and liver. Likewise, reduction in blood pressure may also lead to circulatory insufficiency during the surgical procedures which, unless alleviated, may do serious harm even to patients who have previously exhibited no signs of heart, kidney or liver disfunction.

More recently the amino ketones, particularly acid addition salts thereof, have been advanced as a general anesthetic which does not have the deleterious effects on blood pressure and respiration exhibited by other general anesthetics. The amino ketone, ketamine hydrochloride which is chemically designated as 2-(o-chlorophenyl)-2-(methylamino)cyclohexanone hydrochloride has been accepted as a general anesthetic which does not lower respiration or blood pressure. Ketamine hydrochloride, however, induces a very unpleasant psychological experience in many patients to which it has been administered.

Accordingly, it is an object of this invention to provide a pharmaceutically acceptable general anesthetic which is safe for the patient and which does not adversely effect the patients respiration and blood pressure.

It is another object of this invention to provide a general anesthetic which does not afflict the patient with a recallable unpleasant psychological experience either during administration or recovery from.

Another object of this invention is to provide a therapeutic composition which can be administered to relieve anxiety and to raise the body tolerance for pain without adversely affecting body functions such as blood pressure and respiration.

These and other objects and advantages of this invention will be apparent after a reading of the specification and claims appended thereto.

SUMMARY OF THE INVENTION

The foregoing objects and advantages of this invention are achieved by forming a solution comprising 10 parts by weight of ketamine hydrochloride to one part by weight of diazepam (7-chloro-1,3-dihydro-1-methyl-5-phenyl-2H-1,4-benzodiazepin-2-cne) in an aqueous medium. The solution is stable and remains effective after substantially long storage periods.

When administered in general anesthetic doses, the solution is active as a general anesthetic which is used in a variety of surgical procedures and is compatible with other drugs used during anesthesia and there is no impairment or lowering of respiration, blood pressure and heart action. When used in less than general anesthetic doses, the composition of this invention is effective in lowering anxiety and raising the pain level without substantially impairing any of the normal body functions. In no case were unpleasant psychological experiences able to be recalled.

DESCRIPTION OF THE INVENTION

The novel composition of this invention comprises a pharmaceutically acceptable aqueous solution containing an amino ketone or pharmaceutically acceptable acid addition salt thereof and a tranquilizer or sedative agent. The vehicle for the active ingredients of the composition of this invention is a conventional intravenous carrier consisting of a 5% aqueous dextrose solution containing .11% sodium chloride.

The amino ketone is prepared in accordance with U.S. Pat. No. 3,254,124 and is preferably the hydrochloric acid addition salt of 2-(o-chlorophenyl)-2-(methyl amino) cyclohexanone. As used hereinafter, this material will be identified by its common name ketamine hydrochloride. Ketamine hydrochloride is an excellent general anesthetic which, when used in general surgical procedures, using generally accepted procedures, does not have the adverse effects on body functions, particularly on the respiration, heart and blood functions, which are normally encountered with conventional anesthetics. Unfortunately, ketamine hydrochloride has undesirable psychological side effects on an unacceptably high percentage of patients to whom the material has been administered during surgical procedures.

A tranquilizing or sedative agent is selected for its modifying effect on the ketamine hydrochloride, that is to say, it must alleviate or eliminate the psychological side effects caused by administering of ketamine hydrochloride in the reduction of blood pressure, respiration or other body functions. It must induce in the patient the inability to recall any sensations due to the administration of the ketamine hydrochloride. The tranquilizer or sedative agent and the ketamine hydrochloride must be compatible with each other to form a stable solution in the intravenous carrier.

The preferred tranquilizing and sedative agent used in anesthetic composition of this invention is 7-chloro-1,3-dihydro-1-methyl-5-phenyl-2H-1,4-benzodiazepin-2-one. This material will be referred to hereinafter by its common name, Diazepam. The preparation of this material is described in U.S. Pat. Nos. 3,109,843, 3,136,815 and its purification is described in U.S. Pat. No. 3,102,116.

The relative proportions of ketamine to diazepam in the composition of this invention is maintained on the order of 10 parts of ketamine hydrochloride to one part of diazepam. When the relative proportion of diazepam is increased, administration of the solution begins to affect body functions such as a lowering of blood pressure, presumably, to the action of the diazepam, which, when used alone, lowers body functions. On the other hand, when the proportion of ketamine hydrochloride is increased, patients experience recallable psychollogical side effects due, presumably, to the ketamine hydrochloride.

The anesthetic and sedative solution contains 1.0 mgm of ketamine hydrochloride (about 0.1% by weight) and 0.1 mgm of diazepam (about 0.01% by weight) for each cubic centimeter of intravenous carrier. For convenience of administration the solution is made up in larger quantities; it being preferred to have on hand 500 cc of solution which includes 500 mgm of ketamine hydrochloride and 50 mgm of diazepam.

The solution thus formed is clear and colorless and stable. Even after a three month storage period the solution retains its effectiveness and exhibits no signs of instability such as the formulation of a precipitant or a change of pH.

The anesthetic and sedative composition is administered intravenously and the dosage administered varies with the age, size, general condition and mental state of the patient. The dosage and rate of administration is determined in accordance with standard procedures utilized for conventional anesthetic and sedative or tranquilizing materials. Thus, in using the composition of this invention as a general anesthetic, the anesthesiologist will determine the initial rate of administration in accordance with the age and size of the patient as well as the amount of premedication the patient has received.

The composition of the invention is administered as a total solution, consequently when referring to administration of the solution, rates and quantities will be designated as cc of solution. The milligrams of active ingredients can be readily determined from the volume of total solution.

When using the composition of this invention as a general anesthetic, it has been found that for the average adult patient between 40 cc and 80 cc of solution will render the patient unconscious and ready for surgery. At this point, a nitrous oxide-oxygen mixture is administered along with the composition of this invention in accordance with standard procedure used for general anesthesia. During surgery the rate of administration of the composition of this invention is determined by the requirements of the patient and normally the rate of administration is decreased substantially.

Clinically, the composition of this invention is compatible with all commonly used drugs, barbiturates, muscle relaxants and the like and with other general anesthetics commonly employed in surgical procedures. Thus, patients may be premedicated or sedated prior to arrival at surgery in accordance with standard procedures and using standard preoperative medications.

No special care is required for the patient in the recovery room other than normal recovery room procedure. A small percentage of patients have become talkative and slightly restless during recovery priod. However, when interviewed after full recovery from anesthesia, no patient, who had been administered the composition of this invention, could remember having experienced any unpleasant sensation from the anesthetic.

When used as a general anesthetic, the composition of this invention may be employed in a variety of surgical procedures on a variety of body portions, including, cardiovascular surgery, general surgery, neurosurgery, opthamological surgery, orthopedic surgery, oral surgery, plastic surgery, uriological procedures and gynecological surgery. No special equipment is required for the administration of the composition of this invention as a general anesthetic and any standard measure dose delivery intravenous system may be utilized.

When used as a sedative and an anxiety reducer, the composition of this invention is used in smaller dosages than would be required for general anesthetic purposes. In smaller doses the composition demonstrates an ability to lower anxiety levels and raise the pain threshold of the patient without a reduction in body functions including altering heart action.

The following examples are by way of illustration of preferred embodiments of this invention and they are not intended to limit the invention to the details therein set forth.

EXAMPLE I

To 500 cc of an intravenously administrable solution containing 5% dextrose and 0.11% sodium chloride was added 500 milligrams of ketamine hydrochloride which contained benzethonium chloride in proportions of one part to 10,000 parts ketamine hydrochloride, as a preservative and 50 milligrams of diazepam. The resulting solution was clear and colorless. The solution had a pH of 5.314 when freshly prepared.

The solution was stored in the light at room temperature for three months. At the end of the three month period there was no change in appearance of the solution and it continued to be clear and colorless.

Three samples of the three months old solution were taken and the first sample was centrifuged at high speed for 15 minutes. Examination showed no evidence of precipitation or crystallization.

The second sample was tested for pH which was found to be 5.331. The difference in pH between the three month old sample and the first sample was within experimental error and it was determined that there was no change in pH of the solution, even after standing for three months.

The third sample was checked for the presence of aerobic and anaerobic bacteria and there was no indication of growth after 6 days.

EXAMPLE II

To determine the pharmacological action of the anesthetic solution of this invention in various surgical procedures, the solution was administered as a general anesthetic to 200 patients who were undergoing a variety of surgical procedures on various portions of the body. The types of surgical procedures and the number of patients undergoing each procedure are set forth in Table A below.

Table A

| Surgical Procedure | Number of Patients |
|---|---|
| Cardiovascular | |
| Insertion of permanent Pacemaker | 2 |
| Reconstruction of Internal carotid artery | 2 |
| Carotid angiogram | 3 |
| End arterectomy popliteal artery | 1 |
| Decompression popliteal artery | 1 |
| Bilateral femoral arteriogram | 2 |
| Arch aortogram. Selective carotid angiogram | 3 |
| Control of bleeding carotid endarterectomy | 1 |
| General Surgery | |
| Umbilical herniorrhaphy | 3 |
| Cholecystectomy | 10 |
| Hermorrhoidectomy | 6 |

Table A-continued

| Surgical Procedure | Number of Patients |
|---|---|
| Inquinal hemorrhaphy | 5 |
| Insertion catheter femoral vein | 1 |
| Excision lipomas neck and shoulder | 1 |
| Appendectomy | 3 |
| Excision breast tumor | 5 |
| Mastectomy | 5 |
| Excision condylomata perineum | 1 |
| Gastric resection | 2 |
| Vagotomy, pyloroplasty, cholecystectomy | 1 |
| Cholecystectomy with exploration of common duct | 2 |
| Biopsy tumor of cheek | 1 |
| Splenectomy | 1 |
| Excision tumor anterior chest wall | 2 |
| Cholecysto-jejunostomy, gastro-jejunostomy | 1 |
| Radical excision tumor of abdominal wall | 1 |
| Neurosurgery | |
| Laminectomy | 5 |
| Decompression right median nerve | 1 |
| Pneumoencephalogram | 1 |
| Ophthamology | |
| Correction of ptosis right upper lid | 1 |
| Extraction of cataract | 3 |
| Excision tumor eyelid with plastic repair | 1 |
| Orthopedics | |
| Total hip replacement | 4 |
| Arthrotomy of knee | 4 |
| Open reduction fractured hip | 5 |
| Repair amputation fingers | 2 |
| Lysis of adhesion of shoulder | 1 |
| Osteotomy tibia, bilateral bunionectomy | 1 |
| Repair compound fracture of fingers | 1 |
| Injection and manipulation shoulder | 1 |
| Excision of Duputren's contractual | 1 |
| Open reduction fractured shoulder | 1 |
| Excision ganglion of wrist | 2 |
| Neurolysis and tenolysis index finger | 1 |
| Open reduction fractured ankle | 2 |
| Release contracture sternomastoid muscle | 1 |
| Open reduction fractured patella | 1 |
| Removal Hegie Pins and Ken Nail from hip | 1 |
| Replacement of head and neck of femur with prosthesis | 1 |
| Tenolysis tendons of fingers | 1 |
| Excision ingrown toenail | 1 |
| Repair ruptured quadraceps femoris | 1 |
| Revision amputation of toes | 1 |
| Excision tumor of heel | 1 |
| Section of pulley flexor pollocis longus | 1 |
| Total right knee replacement | 1 |
| Otolaryngoscopy | |
| Bilateral nasal polypectomy | 2 |
| Laryngoscopy, biopsy vocal cords | 3 |
| Bronchoscopy | 1 |
| Laryngoscopy, excision cyst of larynx | 1 |
| Oral Surgery | |
| Multiple extractions | 2 |
| Odondectomy | 3 |
| Removal extosis right biscupid | 1 |
| Plastic Surgery | |
| Abdominal lipectomy and thigh reduction | 1 |
| Urology | |
| Urethral dilatation | 1 |
| Transurethral resection bladder tumor | 4 |
| Transurethral Resection of prostate | 4 |
| Hemi-nephrectomy | 1 |
| Manipulation urethral calculus | 3 |
| Needle biposy prostate | 1 |
| Cystoscopy | 11 |
| Cystoscopy, biopsy prostate | 1 |
| Circumcision | 2 |
| Nephrolithotomy | 1 |
| Excision urethral tumor | 1 |
| Cystoscopy, retrograde Pyelogram | 3 |
| Nephrectomy | 1 |
| Excision and fulguration melanoma urethra | 1 |
| Gynecology | |
| Dilatation and curettage | 17 |
| Excision Bartholin/s cyst | 2 |
| Salpingo-oophorectomy | 1 |
| Therapeutic abortion | 3 |
| Anterior vaginal repair | 1 |
| Anterior and posterior vaginal repair | 5 |
| Total hysterectomy | 5 |
| Bilateral partial salphingectomy | 3 |

In this series of procedures, the youngest patient was five years old and the eldest ninety, with an average age of 57.25 years. The lightest patient weighed 49 pounds, the heaviest weighed 248 pounds, and the average weight of 200 patients was 144.41 pounds. The average duration of anesthesia was 79 minutes and the average dosage of solution was 150 cc. As with conventional anesthetics, the longer the duration of the anesthesia, the greater the volume of general anesthetic administered.

The anesthetic utilized was prepared in accordance with Example I and was administered intravenously using a measured dose delivery system consisting of a Metriset intravenous administration set and pediatric IV set (McGaw Laboratories). A threeway stop cock with extension (Pharmoseal, Inc.) and a 20 gage needle were attached. The delivery system is filled to the 100 cc. mark and the tubing cleared of air. A venopuncture was performed and the solution allowed to run in a steady stream. If the preoperative sedation was heavy, the average adult patient fell asleep after about 40 cc. of the solution had been administered. Where patients were fully awake, it was noted that some experienced strange sensations after about 20 cc. of the anesthetic had been administered. In this event 125 mgms of penothal was administered and sleep readily occurred.

Upon the occurrence of sleep, a face mask was applied and a gas mixture of two liters of oxygen and four liters of nitrous oxide was also administered, and the patient prepared for surgery. By the time, the patient received approximately 80 cc. of the anesthetic solution, surgical anesthesia was achieved and the rate of administration of the solution was slowed to a steady drip and matched against the individual requirements of the patient.

In some cases the patient became light during surgery. In such cases 10 cc. of the solution were administered rapidly and the patient returned to a deep sleep. An alternate procedure was used to continue administration of the anesthetic solution at its normal rate and to administer 50 to 100 mgms of pentothal. In some cases, depending upon the patient's condition and the position required for the surgical procedure, intubation was performed. In all cases, the intubation was performed in the usual manner and was accompanied by administration of succinylcholine. The anesthesia was then conducted in the usual manner. The number of patients requiring intubation was less than when other anesthetic agents were used.

Following surgery on the first 90 patients, it was noted that in general they spent more time in the recovery room than was normal for recovery periods where conventional anesthetics were used. Although this was not considered a serious problem and was not harmful to the patient, it was inconvenient from the standpoint of utilization of recovery room space and recovery room personnel. Consequently, the following 110 patients were treated with 0.4 mgms of naloxone hydrochloride, a conventional narcotic antagonist. Following the introduction in this procedure, the patients spent no more time in the recovery room than when conventional general anesthetics were administered.

No special precautions were taken with the patients in the recovery room. Four patients experienced some form of psychological disturbance during the recovery period.

Later, the patients were interviewed in their rooms and no patient had any recollection of unpleasant experiences caused by the anesthetic.

During all of the surgical procedures, body functions were monitored. In particular, respiration, heart and blood pressure were considered the most important with respect to the use of the anesthetic solution of this invention. In all patients the total volume of respiration increased with no diminution in rate. At no time did apnea occur unless it was intentionally produced by muscle relaxants.

All patients who were undergoing major surgery or were seriously ill, including those with previously known cardiac diseases, were monitored with a cardioscope. No change in rhythm or the complexes was noted in either those patients with a normal or abnormal electrcardiogram. Most patients exhibited an initial rise in systolic blood pressure, but not as frequent or severe as seen with ketamine hydrochloride when used alone. Six patients developed hypotension and they were treated by administering 30 mgms of Wyamine intravenously.

EXAMPLE III

The following test was run to determine the effectiveness of the solution of this invention as a pain and anxiety relieving agent, such as would be used in the treatment of myocardial infarction as compared with ketamine hydrochloride and diazepam used singly.

Change in the level of perception and pain threshold were determined and anxiety artificially induced by applying varying strength electrical current to electrodes attached to two fingers of the right hand. When the current became painful, the subject could signal the experimenter to turn off the current. The maximum current levels were noted and recorded.

Anxiety levels were determined using an audiometer which the subject would set at the level of sound which was most comfortable for him. It has been established that there is a direct correlation in the setting of the sound level and the level of anxiety. The level of sound, as indicated by the audiometer settings, increasing with the level of anxiety.

Anxiety levels and pain thresholds for each subject was first established by running the test on the subject without the administration of sedative. In the first test a solution of 500 mgm of ketamine hydrochloride in 500 cc of the aqueous 5% dextrose, 0.11% NaCL intravenous carrier was administered intravenously at the rate of 30 drops per minute. The pain threshold was elevated over the threshold for the subject without any agent having been administered, however, there was no change in the anxiety level as indicated by the audiometer setting. Upon increasing the rate of administration of the ketamine hydrochloride solution to 60 drops per minute the anxiety level of the subject increased.

50 mgms of diazepam was added to 500 cc of the aqueous 5% dextrose, 0.11% NaCL intravenous carrier was administered intravenously at the rate of 30 drops per minute and the test repeated. There was a drop in the anxiety level but only a slight rise in the pain threshold.

The solution of this invention prepared in accordance with Example I was administered intravenously at a rate of 30 drops per minute. The audiometric test showed a decrease in anxiety and the subject was able to withstand two to four times the intensity of the electrical current over his pain threshold established when no agent is administered. The subject felt relaxed, was able to demonstrate coordination by standing on one foot, comprehend all remarks and perform simple mathematical problems. His vision was not impaired.

When administered in less than general anesthetic quantities, the foregoing test indicates that the solution of this invention increases the pain threshold and reduces the anxiety level of the patient. Likewise, there is no deleterious effect on body functions and particularly on heart blood pressure and respiration. It appears that the solution of this invention is an excellent agent for the treatment of patients where rest and freedom from anxiety are required and where an increase in the pain threshold is indicated. In particular, the solution of this invention is indicated for the treatment of myocardial infarction because the patient is normally in distress, not only from the pain caused by the infarction but also due to anxiety and frustration. In many cases, conventional sedative cannot be prescribed because of the adverse effect on blood pressure and heart action.

I claim:

1. A method for inducing anesthesia in a human patient comprising intraveneously administering to said patient an anesthetizing amount of an aqueous solution of 5% dextrose, 0.11% sodium chloride, 0.1% 2(-o-chlorophenyl)-2-(methylamino) cyclohexanone hydrochloride and 0.01% 7-chloro-1,3-dihydro-1-methyl-5-phenyl-2-H-1,4-benzodiazepin-2-one.

* * * * *

UNITED STATES PATENT AND TRADEMARK OFFICE
CERTIFICATE OF CORRECTION

PATENT NO. : 4,017,619

DATED : April 12, 1977

INVENTOR(S) : Raymond W. Burnap

It is certified that error appears in the above-identified patent and that said Letters Patent are hereby corrected as shown below:

Column 1, line 51, "effect" should be --affect--.
Column 2, line 3, "2-cne" should be --2-one--.
Column 3, line 49, "barbiturate" should be --barbituate--;
line 59, "priod" should be --period--.

Column 7, line 14, "electrcardiogam" should be --electrocardiogram--.

Signed and Sealed this

Sixth Day of December 1977

[SEAL]

Attest:

RUTH C. MASON
Attesting Officer

LUTRELLE F. PARKER
Acting Commissioner of Patents and Trademarks

UNITED STATES PATENT OFFICE
CERTIFICATE OF CORRECTION

Patent No. 4,017,619　　　　　　　　　　Dated　April 12, 1977

Inventor(s)　Raymond W. Burnap

It is certified that error appears in the above-identified patent and that said Letters Patent are hereby corrected as shown below:

Column 6, line 12, after "Metriset" insert -- ® --.

*Signed and Sealed this*

*Twenty-seventh* Day of *December 1977*

[SEAL]

*Attest:*

RUTH C. MASON　　　　　　　LUTRELLE F. PARKER
*Attesting Officer*　　　　*Acting Commissioner of Patents and Trademarks*